(12) United States Patent
Augais

(10) Patent No.: US 10,495,605 B2
(45) Date of Patent: Dec. 3, 2019

(54) DEVICE FOR MEASURING A QUANTITY OF A SUPERPARAMAGNETIC MATERIAL

(71) Applicant: ATWARE, Saint Cyr sous Dourdan (FR)

(72) Inventor: Thierry Augais, Saint Cyr sous Dourdan (FR)

(73) Assignee: ATWARE, Saint Cyr Sous Dourdan (FR)

( * ) Notice: Subject to any disclaimer, the term of this patent is extended or adjusted under 35 U.S.C. 154(b) by 177 days.

(21) Appl. No.: 15/739,934

(22) PCT Filed: Jun. 10, 2016

(86) PCT No.: PCT/FR2016/051408
§ 371 (c)(1),
(2) Date: Dec. 26, 2017

(87) PCT Pub. No.: WO2016/207509
PCT Pub. Date: Dec. 29, 2016

(65) Prior Publication Data
US 2018/0188206 A1  Jul. 5, 2018

(30) Foreign Application Priority Data
Jun. 26, 2015 (FR) .................................... 15 55927

(51) Int. Cl.
*G01N 27/74* (2006.01)
*G01N 33/543* (2006.01)
(Continued)

(52) U.S. Cl.
CPC ....... *G01N 27/745* (2013.01); *G01N 33/5302* (2013.01); *G01N 33/54326* (2013.01); *G01N 33/54346* (2013.01); *H01F 5/04* (2013.01)

(58) Field of Classification Search
CPC ............ G01N 27/745; G01N 33/5302; G01N 33/54326; G01N 33/54346; G01N 27/82;
(Continued)

(56) References Cited

U.S. PATENT DOCUMENTS 6,825,655 B2 * 11/2004 Minchole ............... B82Y 25/00
204/557
8,927,260 B2 * 1/2015 Chin ...................... G01N 33/58
435/287.2
(Continued)

OTHER PUBLICATIONS

Krause et al., "Magnetic particle detection by frequency mixing for immunoassay applications", Journal of Magnetism and Magnetic Materials, 2007, pp. 436-444, vol. 311.
(Continued)

*Primary Examiner* — Patrick Assouad
*Assistant Examiner* — Robert P Alejnikov, Jr.
(74) *Attorney, Agent, or Firm* — Young & Thompson

(57) ABSTRACT

A device for measuring a quantity of a superparamagnetic material includes four coils (1-4) and a unit for injecting, into the coils, a direct current and two alternating currents of different frequencies. The quantity of superparamagnetic material is derived from an amplitude of a component at a mixing frequency, which frequency is a linear combination of the frequencies of the two alternating currents. The device is designed to reduce the influence of stray electromagnetic fields and inadvertent signal offsets on the measurement results. The device may advantageously be used for immunoassays.

20 Claims, 3 Drawing Sheets

Figure 1:
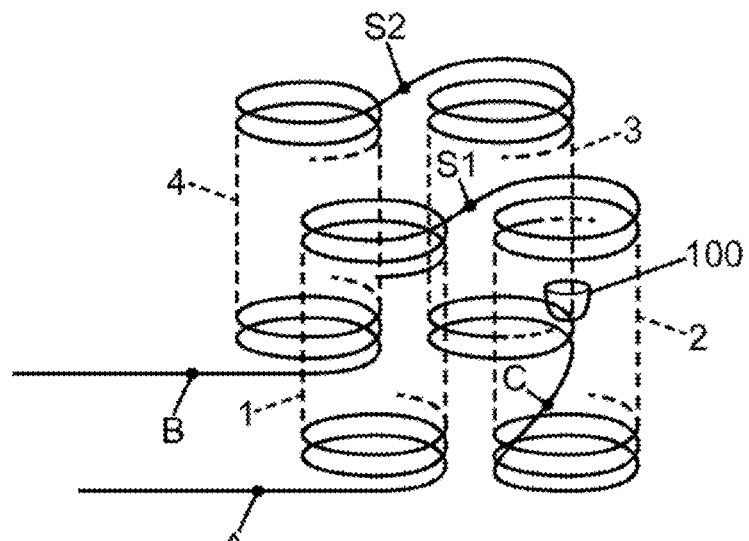

(51) Int. Cl.
  *G01N 33/53* (2006.01)
  *H01F 5/04* (2006.01)
(58) Field of Classification Search
  CPC ........... H01F 5/04; G01F 1/716; G01R 33/00; G01R 33/20; G01R 33/5601; G01R 33/60
  USPC ......................................................... 324/214
  See application file for complete search history.

(56) References Cited

U.S. PATENT DOCUMENTS

| | | | |
|---|---|---|---|
| 2007/0155024 A1* | 7/2007 | Miethe | G01N 27/745 436/524 |
| 2009/0164161 A1* | 6/2009 | Hong | B82Y 5/00 702/75 |
| 2014/0266175 A1* | 9/2014 | Hattersley | G01R 33/0213 324/243 |
| 2015/0022198 A1* | 1/2015 | David | G01D 5/2013 324/251 |
| 2015/0338376 A1* | 11/2015 | Waanders | G01R 33/0017 324/201 |

OTHER PUBLICATIONS

International Search Report, dated Sep. 16, 2016, from corresponding PCT application No. PCT/FR2016/051408.

* cited by examiner

DEVICE FOR MEASURING A QUANTITY OF A SUPERPARAMAGNETIC MATERIAL

The present invention relates to a device for measuring a quantity of a superparamagnetic material, as well as a measurement method using this device.

A superparamagnetic material is a non-linear magnetic material that does not have hysteresis when the magnetic excitation that is applied to this material is varied periodically.

Numerous applications make it necessary to measure quantities of a superparamagnetic material, particularly the performance of immunoassays, known as immunotests. In such immunotests, molecules of an immunological substance such as antibodies or antigens are complexed with beads of a superparamagnetic material and the quantity of immunological substance is determined from measurements of the quantity of superparamagnetic material.

There is then a significant need for devices for measuring quantities of superparamagnetic material that have the following qualities:
the device can be produced at a low cost;
the device generates low energy consumption for each measurement;
the results of the measurements that are performed with the device are not affected, or are only slightly affected, by involuntary signal offsets;
the measurements that are performed with the device have a high signal-to-noise ratio;
the device produces measurement results that are robust with respect to external electromagnetic interference; and
the device must meet the regulatory electromagnetic compatibility (EMC) requirements.

To improve these criteria with respect to existing devices, a first aspect of the present invention proposes a novel device for measuring a quantity of superparamagnetic material, which comprises:
four coils of electrical wire having identical or substantially identical respective geometries and electrical and electromagnetic properties, and these four coils being electrically connected in series so as to form a chain with two end terminals of the chain, a central terminal in the chain, and two secondary terminals of the chain that are each located between the central terminal and one of the two end terminals;
means for injecting a direct current into the chain of coils, which are connected to the two end terminals of the chain of coils, and means for adjusting an intensity of the direct current;
means for injecting a first alternating current having a first frequency, which are connected to inject the first alternating current into the chain of coils through the central terminal, and to recover this first alternating current through the two end terminals, so that the first alternating current flows with first intensities that are identical or substantially identical through the two end terminals without flowing via the secondary terminals;
means for injecting a second alternating current having a second frequency different from the first frequency, that are connected in order to inject the second alternating current into the chain of coils via the two secondary terminals, and to recover this second alternating current through the central terminal and the two end terminals so that the second alternating current flows with second intensities that are identical or substantially identical via the two secondary terminals, and so that this second alternating current flows with third intensities that are identical or substantially identical in all of the coils but in opposite directions between two successive coils in the chain; and
means for detecting at least one voltage component that exists between the two secondary terminals of the chain of coils, with a frequency of this voltage component, called mixing frequency, being a linear combination of the first frequency and the second frequency, with linear combination coefficients that are fixed non-zero integers.

The device of the invention is thus arranged so that when the quantity of superparamagnetic material is located in one of the coils, known as the measuring coil, the detection means output a measurement signal that is proportional to this quantity of superparamagnetic material.

In the device of the invention, the quantity of the superparamagnetic material is determined from the extent of its capacity to produce an alternating voltage at the mixing frequency in at least some of the coils, due to the non-linearity of the superparamagnetic material.

Such a device can be produced using electrical components that are commercially available at low cost, particularly because they are already produced in large quantities for other applications.

The connection of the direct current injection means to the coils, that of the first and second alternating current injection means and that of the detection means reduce or suppress, by their connection direction, offsets that would be present in the measurement signal, so that this measurement signal is indeed proportional to the quantity of the superparamagnetic material.

In addition, the means for injecting the currents can easily be selected or designed to ensure electromagnetic compatibility.

Preferably, the coil in which the quantity of the superparamagnetic material to be measured is located may be one of the two coils that are intermediate between the secondary terminals of the chain of coils.

In order to reduce the interference with the measurements that could be caused by stray electromagnetic radiation, the four coils may advantageously be juxtaposed along an entire length of the coils. Moreover, the two coils that are in between the two secondary coils of the chain of coils may have winding directions that are opposite to each other. Preferably, the other two coils may also have winding directions that are opposite to each other. In this way, stray electromagnetic radiation causes induction voltages in the coils that cancel each other two by two.

Furthermore, a quotient between the first and second frequencies may preferably be greater than 10, so that the means for detecting the voltage component at the mixing frequency isolate this component more efficiently.

In preferred embodiments of a device according to the invention, the direct current injection means, first alternating current injection means and second alternating current injection means may comprise together four connecting cables that are respectively dedicated to each of the four coils. Each of the cables comprises two electrical wires that are connected one by one to the two successive terminals in the chain of coils that directly connect the coil to which this cable is dedicated. Thus, all of the direct current, all of the first alternating current and all of the second alternating current that are injected into the coils are carried out and back by the four cables. The respective lengths of the four cables can then be adjusted so that the third intensities of the second alternating current are identical or substantially identical in absolute terms in all of the coils of the chain.

Moreover, the transfer of electrical energy to the coils, from the means for injecting the alternating current that has the highest frequency, can be improved in this way. For identical measurement sensitivity, the energy consumption of the device can thus be reduced.

Furthermore, when the second frequency is higher than the first frequency, the means for injecting the second alternating current may comprise a source of the second alternating current and a primary winding of a transformer, with a current output of the source that is connected to a middle point of the primary winding of the transformer. In this case, the two end terminals of the primary winding are connected respectively to the two secondary terminals of the chain of coils, and a secondary winding of the transformer belongs to the means for detecting the voltage component that has the mixing frequency. In such an embodiment, the voltage that is transmitted to the detection means has, by design of the device, components at the first and second frequencies that have zero amplitudes. For this reason, the device of the invention can be said to be self-compensated with respect to possible contributions from the excitation signals at the first and second frequencies in the signal that is detected. The component of the mixing frequency can thus be isolated with greater efficiency and purity.

In particular, in order to obtain a signal-to-noise ratio that is higher, the means for detecting the voltage component that has the mixing frequency, in a device according to the invention, may comprise:
- a first synchronous demodulator that is coupled to the means for injecting the second alternating current, and which is arranged in order to offset the frequency of the voltage component that has the mixing frequency, by suppressing a contribution of the second frequency to this mixing frequency; and
- a second synchronous demodulator that is coupled to the means for injecting the first alternating current, and which is arranged in order to offset the frequency of the voltage component that has the mixing frequency, by suppressing a contribution of the first frequency to this mixing frequency.

In this case, these first and second synchronous demodulators are arranged in cascade in order to output a direct electric signal that is proportional to an amplitude of the voltage component that has the mixing frequency. This signal constitutes the measurement signal, after optional amplification. Moreover, when the second frequency is higher than the first frequency, the means for injecting the second alternating current may comprise means of multiplying an instantaneous intensity of the second alternating current by a pseudo-random sequence of factors each equal to +1 or −1, so as to create a modulation of the second alternating current that is also suppressed by the first synchronous demodulator. The signal-to-noise ratio of the device can be further increased in this way.

Optionally, to further increase the sensitivity of the detection means, they may be suitable for detecting an association of two components of the alternating voltage that exists between the two secondary terminals of the chain of coils, corresponding to two separate mixing frequencies. However, in such a case, these two components have opposing contributions for the lowest one of the first and second frequencies in the linear combinations that constitute the two mixing frequencies, and identical contributions for the highest one of the first and second frequencies.

Generally, when the second frequency is higher than the first frequency, the means for injecting the first alternating current may be connected to the central terminal of the chain of coils by a first capacitor that is suitable for conducting alternating current at the first frequency and at the second frequency. Simultaneously, the means for injecting the second alternating current may be connected to each of the two secondary terminals of the chain of coils by a respective second capacitor that is suitable for conducting alternating current at the second frequency but not at the first frequency. Such an embodiment of the device contributes to ensuring the desired distribution of the direct current, the first alternating current and the second alternating current in the four coils.

A second aspect of the invention proposes a method for measuring an unknown quantity of a superparamagnetic material that comprises the following steps:
- /1/ using a device according to the first aspect of the invention, and with a value of the intensity of the direct current, and respective intensity values for the first alternating current and for the second alternating current, obtaining the measurement signal that is outputted by the detection means when a reference quantity of the superparamagnetic material is located in the measuring coil; and
- /2/ using the same device, the same value of the intensity of the direct current as in step /1/, and the same intensity values as in step /1/ for the first alternating current and for the second alternating current, obtaining the measurement signal that is outputted by the detection means when the unknown quantity of the superparamagnetic material is located in the measuring coil instead of the reference quantity.

The sequence of steps /1/ and /2/ is performed several times, varying the value of the intensity of the direct current between each performance of this sequence. However, the intensity value of the first alternating current and that of the second alternating current are not modified between the successive performances of steps /1/ and /2/. The method then comprises the following steps:
- /3/ forming a first vector with values of the measurement signals that have been outputted successively by the detection means during the performances of step /1/,
- /4/ forming a second vector with values of the measurement signals that have been outputted successively by the detection means during the performances of step /2/; and
- /5/ calculating the unknown quantity of the superparamagnetic material by multiplying the reference quantity by a scalar product of the first vector and the second vector, divided by a scalar product of the first vector and itself.

Preferably, the values of the intensity of the direct current that are used for the successive performances of the sequence of steps /1/ and /2/ may have a mean value that is zero or substantially zero. Thus, direct offsets that would be caused in the measurement results by the direct current injection means, or by the means for injecting the first and second alternating currents, are reduced or suppressed by the mean effect.

In particular, the method of the invention may be used for immunotests or immunoassays. For such applications of the invention, the superparamagnetic material may be complexed with a biomedical or biological substance, in particular with an immunological substance, and particularly with an antibody or an antigen.

Figure 4:
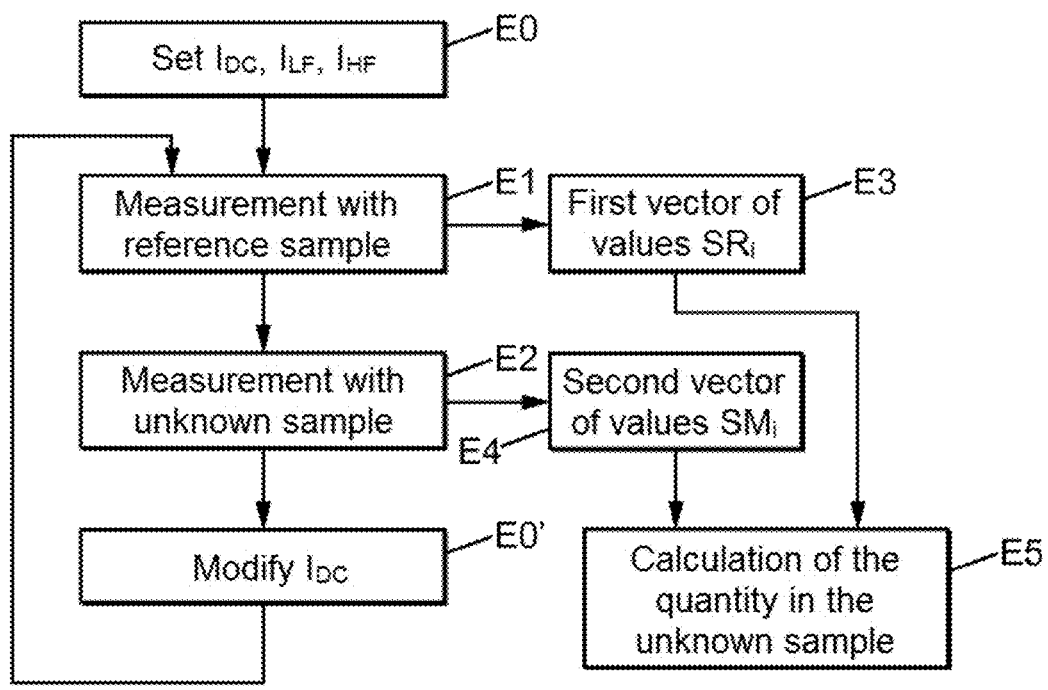
Figure 2:
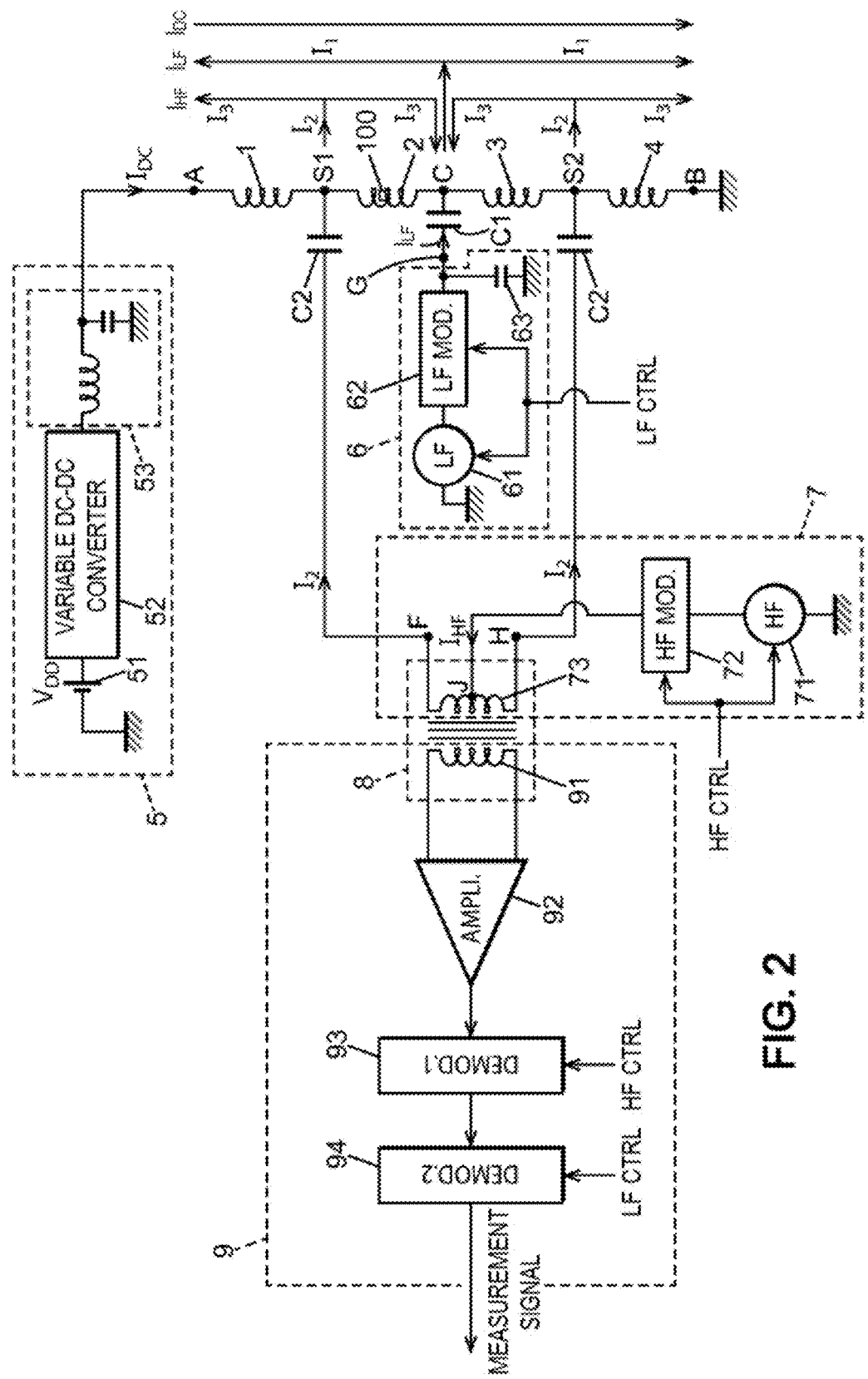
Figure 3:
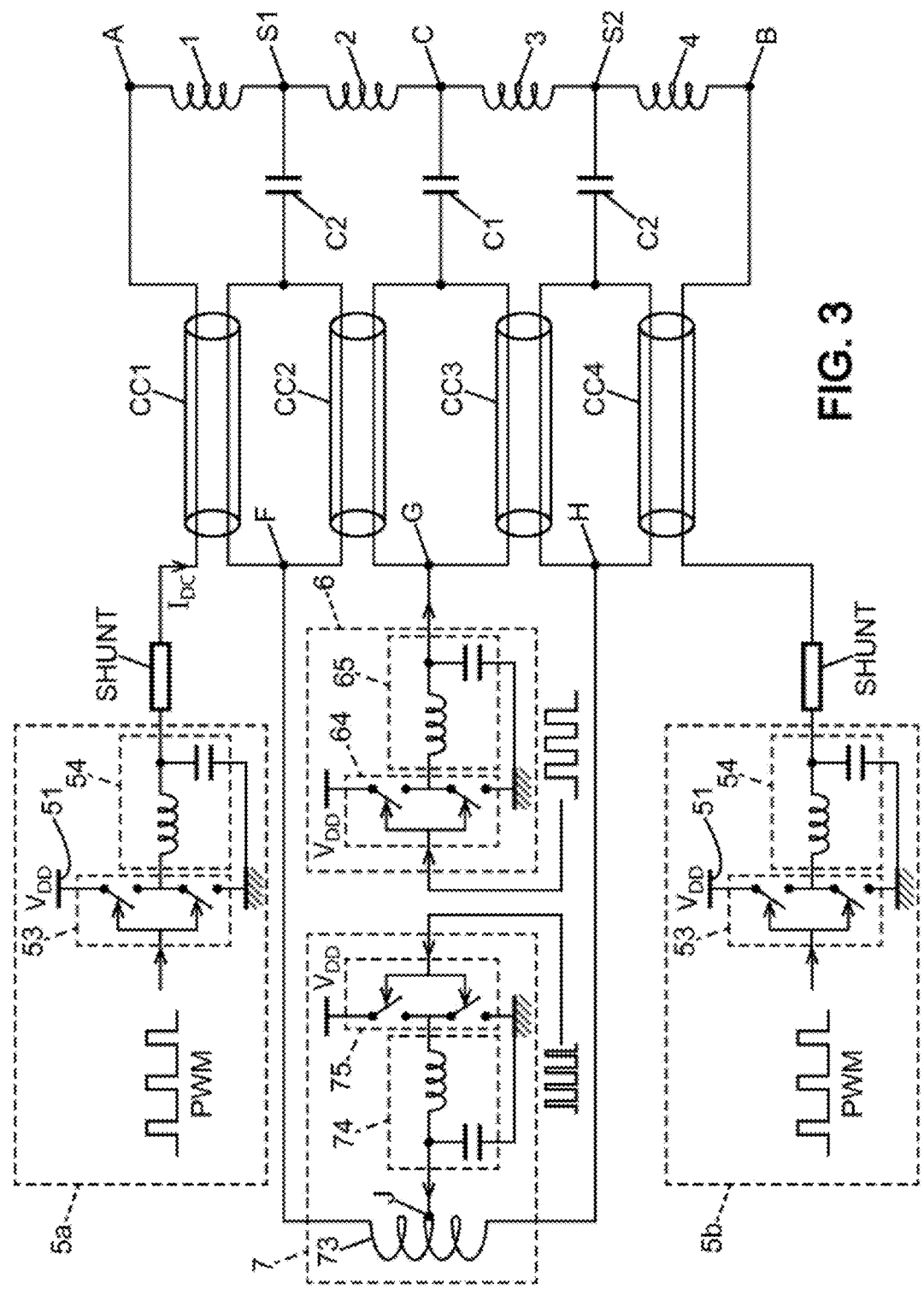

Further features and advantages of the present invention will become apparent from the following description of non-limitative embodiments, with reference to the attached drawings, in which:

FIG. 1 is a perspective view of the four coils of a device according to the invention, FIG. 2 is an overview diagram of a device according to the invention;

FIG. 3 corresponds to FIG. 2 for specific embodiments of the means for injecting the currents; and FIG. 4 is an overview diagram of a method for measuring a quantity of a superparamagnetic material, using a device according to the invention.

For the purpose of clarity of FIG. 1, the apparent dimensions of the components shown do not correspond to actual dimensions or dimension ratios. Furthermore, identical references that are indicated in FIGS. 1 to 3 denote identical components or components with identical functions.

In FIG. 1, reference numbers 1 to 4 denote four coils of electrical wire that are designed to be identical. They may be arranged spatially in any way in relation to each other, but the arrangement of these coils side-by-side and parallel to each other makes it possible to compensate between the coils for the stray voltages that are induced by external electromagnetic radiation. The coils 1 to 4 are electrically connected in series, with winding directions of the electric wire in each coil that may advantageously be opposite to each other between two successive coils in the series connection. A and B respectively denote the end terminals of the series connection of the coils 1-4, terminal A being on the side of coil 1 and terminal B being on the side of coil 4. S1 and S2, called secondary terminals, are respectively placed between coils 1 and 2 and between coils 3 and 4, and C, called the central terminal, is placed between coils 2 and 3. A recess is made in one of the coils, for example in coil 2, in order to insert a sample 100 of superparamagnetic material in a location that is fixed in the coil. This coil in which the sample is placed has been called the measurement coil in the general part of the description.

The designations used in the general part of the present description have the following correspondences with those used for the embodiment in FIGS. 2 and 3: the first frequency may be equal to 1 kHz for example and is denoted LF, and the second frequency may be equal to 200 kHz and is denoted HF. These values of the LF and HF frequencies make it possible to use filters that are commercially available, particularly for radio applications. The first and second alternating currents, which respectively have the frequencies LF and HF, are denoted $I_{LF}$ and $I_{HF}$. The direct current is denoted $I_{DC}$.

The following reference numbers, which appear in FIG. 2, have the meanings given below:

5 generator of the direct current $I_{DC}$, called direct current injection means;
6 generator of the current $I_{LF}$, called first alternating current injection means;
7 generator of the current $I_{HF}$, called second alternating current injection means;
8 transformer, with a primary winding with reference 73 and a secondary winding with reference 91;
9 means for detecting an alternating voltage component that exists between the secondary terminals S1 and S2, with a mixing frequency that is a linear combination of the frequencies LF and HF;
C1 capacitor sized to transmit the current $I_{LF}$, and which also transmits a current at the frequency HF as a result; and
C2 capacitors sized to transmit currents at the frequency HF, but to prevent currents at the frequency LF from passing through.

The generator 5 may be made up of a direct voltage source 51, a variable DC-DC converter 52 and a filter 53. $V_{DD}$ is the direct voltage produced by the source 51. The converter 52 can be controlled by an operator to adjust the value of the intensity of the current $I_{DC}$ to a desired value, and then to vary this value in order to take a series of successive measurements. The filter 53 ensures that the currents at the frequencies LF and HF can flow outside the coils 1-4 via the end terminal A. The generator 5 produces the current $I_{DC}$.

The generator 6 may be made up of a source of alternating current at the frequency LF, with reference 61, and optionally a modulator 62, denoted LF MOD. When used, the modulator 62 is connected in series to the output of the source 61. LF CTRL denotes a control signal or a source signal of the generator 6. The output of the source 61, or the modulator 62, is connected to the central terminal C by means of the capacitor C1. The capacitor 63 ensures that a current at the frequency HF can flow outside the coils 1-4 via terminal C. The generator 6 produces the current $I_{LF}$.

The generator 7 may be made up of a source of alternating current at the frequency HF, with reference 71, optionally a modulator 72, denoted HF MOD., and the primary winding 73 of the transformer 8. When used, the modulator 72 is connected in series to the output of the source 71. HF CTRL denotes a control signal or a source signal of the generator 7. The output of the source 71, or the modulator 72, is connected to a middle point J of the primary winding 73 of the transformer 8. The end terminals F and H of the primary winding 73 are connected to the secondary terminals S1 and S2 of the chain of coils 1-4, respectively, by means of the capacitors C2. The generator 7 produces the current $I_{HF}$.

Thanks to these connections, the direct current $I_{DC}$, a portion $I_1$ of the intensity of the current $I_{LF}$ and also a portion $I_3$ of the intensity of the current $I_{HF}$ pass through each of the four coils 1-4, with the current orientations that are shown in the right-hand part of FIG. 2. Moreover, the portions of intensities $I_1$ and $I_3$ of the two alternating currents are: $I_1=I_{LF}/2$ and $I_3=I_{HF}/4$. In addition, the current $I_{HF}$ is injected into the chain of coils 1-4 with an intensity $I_2=I_{HF}/2$ via each of the secondary terminals S1 and S2.

The detection means 9 comprise the secondary winding 91 of the transformer 8, an amplifier 92, denoted AMPLI., a first synchronous demodulator 93, denoted DEMOD. 1 and a second synchronous demodulator 94, denoted DEMOD. 2.

The synchronous demodulator 93 receives as an input the voltage that exists at the terminals of the secondary winding 91, after amplification of this voltage, and simultaneously receives the HF CTRL signal that is introduced into the generator 7. It is suitable for carrying out a frequency transfer on the component of the voltage in the secondary winding 91 that has the frequency HF−LF, and advantageously also on the component of the same voltage that has the frequency HF+LF. Preferably, the synchronous demodulator 93 may be of the analogue type. When the modulator 72 is used, the modulation of the current $I_{HF}$ that is produced by this modulator 72 is automatically taken into account by the synchronous demodulator 93. For example, this modulation of the current $I_{HF}$ may consist of reversing the direction of the current $I_{HF}$ repeatedly, according to a random or pseudo-random time sequence. Such current reversals amount to multiplying the current $I_{HF}$ by successive factors each equal to +1 or −1 for variable durations, and produce a spectrum spread of the current $I_{HF}$ as this current is delivered by the generator 7.

Advantageously, the signal that is outputted by the synchronous demodulator 93 may be amplified before it is introduced into the synchronous demodulator 94.

The synchronous demodulator 94 therefore receives as an input the signal outputted by the synchronous modulator 93, after optional amplification, and simultaneously receives the LF CTRL signal that is introduced into the generator 6. It is suitable for carrying out a frequency transfer on the signal outputted by the synchronous demodulator 93. Preferably, the synchronous demodulator 94 may be of the digital type. When the modulator 62 is used, the modulation of the current $I_{LF}$ that is produced by this modulator 62 is automatically taken into account by the synchronous demodulator 94.

In this way, the detection means 9 output a direct voltage that is proportional to the amplitude of the component at the frequency HF–LF, contained in the voltage that exists between the secondary terminals S1 and S2. This component at the frequency HF–LF results from the non-linear behaviour of the superparamagnetic material of the sample 100. Due to this non-linear behaviour, the response of the superparamagnetic material to the simultaneous excitations according to the two frequencies HF and LF contains signals at frequencies that are linear combinations of the two frequencies HF and LF, with linear combination coefficients that are integers. In the present case, the synchronous demodulators 93 and 94 select the combination that is the difference HF–LF. The amplitude of the component at this frequency HF–LF is then proportional to the quantity of superparamagnetic material that is contained in the sample 100. This amplitude constitutes the measurement signal, and can be evaluated by a voltmeter.

FIG. 3 shows possible embodiments of the generators 5-7 that are particularly cost-effective, and a way of connecting them to the coils 1-4 that makes it possible to improve the energy transfer from the generators 5-7 to the coils 1-4.

The direct current generator 5 may be made up of two generators 5a and 5b that are identical but connected respectively to the terminals A and B so that they can inject the direct current $I_{DD}$ into the chain of coils from terminal A towards terminal B or in the opposite direction. Only one of the two generators 5a and 5b is therefore activated for each measurement, depending on the desired sign for the current $I_{DD}$. Each generator 5a, 5b comprises two commutators that are connected in series between the two terminals ($V_{DD}$ and earth) of the source 51. Such an assembly, denoted by the reference 54, is commonly known as a "bridge arm" by a person skilled in the art. It is intended for a chopping function. The intermediate terminal between the two commutators of each generator 5a, 5b is connected to the output of this generator by means of the filter 53. Controlling the commutators by pulse width modulation (PWM) makes it possible to adjust the absolute value of the direct current intensity $I_{DC}$. Resistors, denoted SHUNT, may be inserted in series between the output of each generator 5a, 5b and the chain of coils 1-4.

The alternating current generator 6 may also be produced using a bridge arm, reference 64, and a suitable filter 65. The bridge arm of the generator 6 may also be powered by the source 51, and its two commutators are controlled alternately at the frequency LF. The filter 65, denoted LF filter, selects the fundamental component for output transmission to the central terminal C.

Finally, the alternating current generator 7 may also be produced using a bridge arm, reference 74, and a suitable filter 75. The bridge arm of the generator 7 may equally be powered by the source 51, and its two commutators are controlled alternately at the frequency HF. The filter 75 selects a spectral interval around the fundamental component for output transmission to the secondary terminals S1 and S2. In a known manner, such a composition of the generator 7 makes it possible to simply perform spectrum spread modulation, by offsetting the control pulses of the bridge arm by a half-period according to a random time sequence.

The outputs of the generators 5a, 5b and 6, together with the two end terminals F and H of the primary winding 73 of the transformer 8, may be connected to the terminals A, B, C and S1, S2 by four two-wire cables CC1-CC4. The four cables CC1-CC4 are advantageously of one and the same type, two-wire or coaxial, preferably shielded and with controlled characteristic impedance. They are connected in the following manner:

the first wire of the cable CC1 connects the output of the generator 5a to terminal A of the chain of coils 1-4;

the second wire of the cable CC1 and the first wire of the cable CC2 are connected in parallel in order to connect the end terminal F of the primary winding of the transformer 8 to the secondary terminal S1 of the chain of coils 1-4, by means of the first capacitor C2;

the second wire of the cable CC2 and the first wire of the cable CC3 are connected in parallel in order to connect the output G of the generator 6 to the central terminal C of the chain of coils 1-4, by means of the capacitor C1, the second wire of the cable CC3 and the first wire of the cable CC4 are connected in parallel in order to connect the end terminal H of the primary winding of the transformer 8 to the secondary terminal S2 of the chain of coils 1-4, by means of the second capacitor C2; and the second wire of the cable CC4 connects the output of the generator 5b to terminal B of the chain of coils 1-4.

The respective lengths of the cables CC1-CC4 can then be advantageously selected in order to adjust the connection impedances that are effective for the alternating current $I_{HF}$. Thus, it is possible to increase the electrical energy that is transferred by the generator 7 to the coils 1-4 for equivalent consumption of the device.

With reference to FIG. 4, a first step E0 of a method for measuring a quantity of a superparamagnetic material consists in setting an initial value for the intensity of the current $I_{DC}$, and values for the intensities of the currents $I_{LF}$ and $I_{HF}$. These last two values, for $I_{LF}$ and $I_{HF}$, are used without modification throughout the method.

Step E1 consists in taking a first measurement with a reference sample of the superparamagnetic material. The reference sample is therefore placed in the coil 2. The quantity of superparamagnetic material that is contained in this reference sample is assumed to be known, for example by a mass value that is denoted $M_0$. The value of the measurement signal that is obtained for this first measurement is denoted $SR_1$.

Step E2 is identical to step E1, but replacing the reference sample by the sample to be measured in coil 2. In simple uses of the invention, the sample to be measured and the reference sample contain the same superparamagnetic material. However, the quantity that is contained in the sample to be measured is unknown, and the purpose of the method is to determine it with maximum reliability. The value of the measurement signal that is obtained for this second measurement is denoted $SM_1$.

During step E0', the value of the intensity of the current $I_{DC}$ is modified, then steps E1 and E2 are repeated with this new value for $I_{DC}$. Measurement signal values $SR_2$ and $SM_2$ are then obtained for the reference sample and for the sample to be measured respectively.

Step E0', E1 and E2 are repeated again, for a total of N performances of the sequence of steps E1 and E2, N being an non-negative integer greater than 1. The measurement signal values $SR_i$ and $SM_i$ are then obtained for the reference sample and the sample to be measured respectively, on each performance i of the signal, i being an integer from 1 to N. Preferably, the values that are selected for the current $I_{DC}$ for the performances of steps E0 and E0' have a zero or substantially zero mean value. By "substantially zero mean value" is meant a mean value that is smaller than most of the values that have been selected for the current $I_{DC}$, in absolute terms.

In step E3, a first vector SR is constructed that is constituted by the values $SR_i$, relating to the reference sample: $SR=[SR_i]$.

In the same way, in step E4, a second vector SM is constructed that is constituted by the values $SM_i$, relating to the sample to be measured: $SM=[SM_i]$.

Step E5 then consists in calculating the mass M of superparamagnetic material that is contained in the sample to be measured, from the two value vectors that were constructed in steps E3 and E4. The mass M can thus be calculated using the formula:

$$M=M_0 \cdot (SR \times SM)/(SR \times SR),$$

where × denotes the scalar product of two vectors.

It is understood that the invention can be reproduced by modifying the secondary aspects thereof with respect to the detailed description provided above, while retaining at least some of the advantages cited. These modifications include, but are not limited to:
  the relative positions and orientations of the four coils 1-4 may be changed;
  the use of the modulators 62 and 72 may be combined with the production of the generators 6 and 7 using bridge arms;
  the generators 5, 6 and 7 may have compositions different from those described in relation to FIGS. 2 and 3; and
  the mixture of frequencies that is selected by the detection means 9 in order to obtain the measurement signal may be a linear combination of the frequencies LF and HF other than the difference HF−LF and the sum HF+LF.

The invention claimed is:

1. Device for measuring a quantity of a non-linear magnetic material devoid of hysteresis, known as a superparamagnetic material, the device comprising:
  four coils (1-4) of electrical wire having identical or substantially identical respective geometries and electrical and electromagnetic properties, and the four coils being electrically connected in series so as to form a chain with two end terminals (A, B) of said chain, a central terminal (C) in said chain, and two secondary terminals (S1, S2) of said chain that are each located between the central terminal and one of the two end terminals,
  means (5) for injecting a direct current ($I_{DC}$) into the chain of coils (1-4), connected to the two end terminals (A, B) of the chain of coils, and means for adjusting an intensity of the direct current;
  means (6) for injecting a first alternating current ($I_{LF}$) having a first frequency (LF), connected to inject said first alternating current into the chain of coils (1-4) through the central terminal (C), and to recover said first alternating current through the two end terminals (A, B), so that the first alternating current flows with first intensities ($I_1$) that are identical or substantially identical through said two end terminals without flowing via the secondary terminals (S1, S2);
  means (7) for injecting a second alternating current ($I_{MF}$) having a second frequency (HF) that is different from the first frequency (LF), connected to inject said second alternating current into the chain of coils (1-4) via the two secondary terminals (S1, S2), and to recover said second alternating current through the central terminal (C) and the two end terminals (A, B) so that the second alternating current flows with second intensities ($I_2$) that are identical or substantially identical via said two secondary terminals, and so that said second alternating current flows with third intensities ($I_3$) that are identical or substantially identical in all of the coils but in opposite directions between two successive coils in the chain; and
  means (9) for detecting at least one voltage component that exists between the two secondary terminals (S1, S2) of the chain of coils (1-4), with a frequency of said voltage component, called mixing frequency, being a linear combination of the first frequency (LF) and the second frequency (HF), with linear combination coefficients that are fixed non-zero integers,
so that when the quantity of superparamagnetic material is located in one (2) of the coils (1-4), known as the measuring coil, the detection means (9) output a measurement signal that is proportional to said quantity of superparamagnetic material.

2. Device according to claim 1, in which the four coils (1-4) are juxtaposed along an entire length of the coils, and the two coils (2, 3) that are in between the two secondary terminals (S1, S2) of the chain of coils have winding directions that are opposite to each other.

3. Device according to claim 2, in which a quotient between the first (LF) and second (HF) frequencies is greater than 10.

4. Device according claim 2, in which the means (5) for injecting the direct current ($I_{DC}$), the means (6) for injecting the first alternating current ($I_{LF}$) and the means (7) for injecting the second alternating current ($I_{HF}$) together comprise four connection cables (CC1-CC4) that are respectively dedicated to each of the four coils (1-4), each cable comprising two electrical wires connected one-by-one to the two successive terminals in the chain of coils that directly connect the coil to which said cable is dedicated, so that all of the direct current, all of the first alternating current and all of the second alternating current that are injected into the coils are transported out and back by said cables, and respective lengths of said cables are adjusted so that the third intensities ($I_3$) of the second alternating current ($I_{HF}$) are identical or substantially identical in absolute terms in all the coils in the chain.

5. Device according to claim 2, in which the second frequency (HF) is higher than the first frequency (LF),
  and in which the means (7) for injecting the second alternating current ($I_{HF}$) comprise a source (71) of the second alternating current and a primary winding (73) of a transformer (8), a current output of said source being connected to a middle point (J) of the primary winding of the transformer, and two end terminals (F, H) of said primary winding being connected respectively to the two secondary terminals (S1, S2) of the chain of coils (1-4),
  and in which a secondary winding (91) of the transformer (8) belongs to the means (9) for detecting the voltage component that has the mixing frequency.

6. Device according to claim 2, in which the means (9) for detecting the voltage component that has the mixing frequency comprise:
- a first synchronous demodulator (93) that is coupled to the means (7) for injecting the second alternating current ($I_{HF}$), and which is arranged in order to offset the frequency of the voltage component that has the mixing frequency, by suppressing a contribution of the second frequency (HF) to said mixing frequency; and
- a second synchronous demodulator (94) that is coupled to the means (6) for injecting the first alternating current ($I_{LF}$), and which is arranged in order to offset the frequency of the voltage component that has the mixing frequency, by suppressing a contribution of the first frequency (LF) to said mixing frequency, said first (93) and second (94) synchronous demodulators being arranged in cascade so as to output a direct electric signal that is proportional to an amplitude of the voltage component that has the mixing frequency.

7. Device according to claim 1, in which a quotient between the first (LF) and second (HF) frequencies is greater than 10.

8. Device according claim 7, in which the means (5) for injecting the direct current ($I_{DC}$), the means (6) for injecting the first alternating current ($I_{LF}$) and the means (7) for injecting the second alternating current ($I_{HF}$) together comprise four connection cables (CC1-CC4) that are respectively dedicated to each of the four coils (1-4), each cable comprising two electrical wires connected one-by-one to the two successive terminals in the chain of coils that directly connect the coil to which said cable is dedicated, so that all of the direct current, all of the first alternating current and all of the second alternating current that are injected into the coils are transported out and back by said cables, and respective lengths of said cables are adjusted so that the third intensities ($I_3$) of the second alternating current ($I_{HF}$) are identical or substantially identical in absolute terms in all the coils in the chain.

9. Device according claim 7, in which the second frequency (HF) is higher than the first frequency (LF),
and in which the means (7) for injecting the second alternating current ($I_{HF}$) comprise a source (71) of the second alternating current and a primary winding (73) of a transformer (8), a current output of said source being connected to a middle point (J) of the primary winding of the transformer, and two end terminals (F, H) of said primary winding being connected respectively to the two secondary terminals (S1, S2) of the chain of coils (1-4),
and in which a secondary winding (91) of the transformer (8) belongs to the means (9) for detecting the voltage component that has the mixing frequency.

10. Device according to claim 7, in which the means (9) for detecting the voltage component that has the mixing frequency comprise:
- a first synchronous demodulator (93) that is coupled to the means (7) for injecting the second alternating current ($I_{HF}$), and which is arranged in order to offset the frequency of the voltage component that has the mixing frequency, by suppressing a contribution of the second frequency (HF) to said mixing frequency; and
- a second synchronous demodulator (94) that is coupled to the means (6) for injecting the first alternating current ($I_{LF}$), and which is arranged in order to offset the frequency of the voltage component that has the mixing frequency, by suppressing a contribution of the first frequency (LF) to said mixing frequency, said first (93) and second (94) synchronous demodulators being arranged in cascade so as to output a direct electric signal that is proportional to an amplitude of the voltage component that has the mixing frequency.

11. Device according claim 1, in which the means (5) for injecting the direct current ($I_{DC}$), the means (6) for injecting the first alternating current ($I_{LF}$) and the means (7) for injecting the second alternating current ($I_{HF}$) together comprise four connection cables (CC1-CC4) that are respectively dedicated to each of the four coils (1-4), each cable comprising two electrical wires connected one-by-one to the two successive terminals in the chain of coils that directly connect the coil to which said cable is dedicated, so that all of the direct current, all of the first alternating current and all of the second alternating current that are injected into the coils are transported out and back by said cables, and respective lengths of said cables are adjusted so that the third intensities ($I_3$) of the second alternating current ($I_{HF}$) are identical or substantially identical in absolute terms in all the coils in the chain.

12. Device according to claim 11, in which the second frequency (HF) is higher than the first frequency (LF),
and in which the means (7) for injecting the second alternating current ($I_{HF}$) comprise a source (71) of the second alternating current and a primary winding (73) of a transformer (8), a current output of said source being connected to a middle point (J) of the primary winding of the transformer, and two end terminals (F, H) of said primary winding being connected respectively to the two secondary terminals (S1, S2) of the chain of coils (1-4),
and in which a secondary winding (91) of the transformer (8) belongs to the means (9) for detecting the voltage component that has the mixing frequency.

13. Device according to claim 11, in which the means (9) for detecting the voltage component that has the mixing frequency comprise:
- a first synchronous demodulator (93) that is coupled to the means (7) for injecting the second alternating current ($I_{HF}$), and which is arranged in order to offset the frequency of the voltage component that has the mixing frequency, by suppressing a contribution of the second frequency (HF) to said mixing frequency; and
- a second synchronous demodulator (94) that is coupled to the means (6) for injecting the first alternating current ($I_{LF}$), and which is arranged in order to offset the frequency of the voltage component that has the mixing frequency, by suppressing a contribution of the first frequency (LF) to said mixing frequency, said first (93) and second (94) synchronous demodulators being arranged in cascade so as to output a direct electric signal that is proportional to an amplitude of the voltage component that has the mixing frequency.

14. Device according to claim 1, in which the second frequency (HF) is higher than the first frequency (LF),
and in which the means (7) for injecting the second alternating current ($I_{HF}$) comprise a source (71) of the second alternating current and a primary winding (73) of a transformer (8), a current output of said source being connected to a middle point (J) of the primary winding of the transformer, and two end terminals (F, H) of said primary winding being connected respectively to the two secondary terminals (S1, S2) of the chain of coils (1-4),
and in which a secondary winding (91) of the transformer (8) belongs to the means (9) for detecting the voltage component that has the mixing frequency.

15. Device according to claim 1, in which the means (9) for detecting the voltage component that has the mixing frequency comprise:

a first synchronous demodulator (93) that is coupled to the means (7) for injecting the second alternating current ($I_{HF}$), and which is arranged in order to offset the frequency of the voltage component that has the mixing frequency, by suppressing a contribution of the second frequency (HF) to said mixing frequency; and a second synchronous demodulator (94) that is coupled to the means (6) for injecting the first alternating current (ILF) and which is arranged in order to offset the frequency of the voltage component that has the mixing frequency, by suppressing a contribution of the first frequency (LF) to said mixing frequency, said first (93) and second (94) synchronous demodulators being arranged in cascade so as to output a direct electric signal that is proportional to an amplitude of the voltage component that has the mixing frequency.

16. Device according to claim 15, in which the second frequency (HF) is higher than the first frequency (LF), and the means (7) for injecting the second alternating current ($I_{HF}$) comprise means of multiplying an instantaneous intensity of said second alternating current by a pseudo-random sequence of factors each equal to +1 or −1, so as to create a modulation of said second alternating current that is also suppressed by the first synchronous demodulator (93).

17. Device according to claim 1, in which the second frequency (HF) is higher than the first frequency (LF), and the means (6) for injecting the first alternating current ($I_{LF}$) are connected to the central terminal (C) of the chain of coils (1-4) by a first capacitor (C1) suitable for conducting alternating current at the first frequency (LF) and at the second frequency (HF);

and the means (7) for injecting the second alternating current ($I_{HF}$) are connected to each of the two secondary terminals (S1, S2) of the chain of coils (1-4) by a respective second capacitor (C2) suitable for conducting alternating current at the second frequency (HF) but not at the first frequency (LF).

18. Method for measuring an unknown quantity of a superparamagnetic material, comprising the following steps:

/1/ using a device according to claim 1, and with a value of the intensity of the direct current (IDC), and respective intensity values for the first alternating current (ILF) and for the second alternating current (IHF), obtaining the measurement signal that is outputted by the detection means (9) when a reference quantity of the superparamagnetic material is located in the measuring coil (2); and /2/ using the same device, and the same value of the intensity of the direct current (IDC) as in step/1/, and the same intensity values as in said step/1/ for the first alternating current (ILF) and for the second alternating current (IHF), obtaining the measurement signal that is outputted by the detection means (9) when the unknown quantity of the superparamagnetic material is located in the measuring coil (2) instead of the reference quantity;

performing the sequence of steps /1/ and /2/ two or more times, varying the value of the intensity of the direct current (IDC) between each performance of said sequence, but without modifying the intensity values of the first alternating current (ILF) and the second alternating current (IHF); then:

/3/ forming a first vector with values (SRi) of the measurement signals that have been outputted successively by the detection means (9) during the performances of step /1/;

/4/ forming a second vector with values (SMi) of the measurement signals that have been outputted successively by the detection means (9) during the performances of step /2/; and /5/ calculating the unknown quantity of the superparamagnetic material by multiplying the reference quantity by a scalar product of the first vector and the second vector, divided by a scalar product of the first vector and itself.

19. Method according to claim 18, wherein the values of the intensity of the direct current ($I_{DC}$) that are used for the successive performances of the sequence of steps /1/ and /2/ have a mean value that is zero or substantially zero.

20. Method according to claim 18, wherein the superparamagnetic material is complexed with a biomedical or biological substance, in particular with an immunological substance, and particularly with an antibody or an antigen.

* * * * *